United States Patent [19]
Doiron et al.

[11] Patent Number: 5,269,777
[45] Date of Patent: Dec. 14, 1993

[54] DIFFUSION TIP FOR OPTICAL FIBERS

[75] Inventors: Daniel R. Doiron, Santa Ynez; Hugh L. Narciso, Jr., Santa Barbara, both of Calif.

[73] Assignee: PDT Systems, Inc., Goleta, Calif.

[21] Appl. No.: 853,338

[22] Filed: Mar. 16, 1992

Related U.S. Application Data

[63] Continuation of Ser. No. 608,006, Nov. 1, 1990, abandoned.

[51] Int. Cl.$^5$ .............................................. A61B 17/36
[52] U.S. Cl. ........................................ 606/7; 606/15; 606/16
[58] Field of Search ................ 606/2, 7, 13-16; 128/355-378; 359/31; 385/115-119

[56] References Cited

U.S. PATENT DOCUMENTS

| | | | |
|---|---|---|---|
| 4,322,164 | 3/1982 | Shaw et al. | 356/243 |
| 4,336,809 | 6/1982 | Clark | 606/15 |
| 4,660,925 | 4/1987 | McCaughan | 350/96.15 |
| 4,693,556 | 9/1987 | McCaughan | 350/320 |
| 4,736,743 | 4/1998 | Dakiuzono | 606/16 |

OTHER PUBLICATIONS

Wagineres et al., "Photodynamic Therapy of early cancer . . . ", SPIE Inst. Series vol. IS6 (1990).

Primary Examiner—Peter A. Aschenbrenner
Attorney, Agent, or Firm—Michael G. Petit

[57] ABSTRACT

A cylindrical diffuser tip for use with an optical fiber is described. The diffuser tip comprises a silicone core abutted to the terminus of the conventional optical core of an optical fiber, an outer layer of silicone plus a suitable scatterer, and a final cladding of plastic tubing to provide controlled stiffness or rigidity to the silicone diffuser tip while maintaining a flexibility comparable to the optical fiber. The tip provides a substantially uniform distribution of radiance along its length and is particularly useful for laser radiation treatment of tumors. The stiffness of the diffuser tip can be varied by choosing an outer tubing of varying wall thickness and durometer. The diffuser tip is useful for providing uniform cylindrical illumination of target tissue in remote areas of the body and is particularly useful in such areas as Photodynamic Therapy of tumors and atheromas and hyperthermia.

7 Claims, 2 Drawing Sheets

DIFFUSION TIP FOR OPTICAL FIBERS

CROSS-REFERENCE TO RELATED APPLICATIONS

This is a continuation of application Ser. No. 07/608,006, filed Nov. 1, 1990, now abandoned.

BACKGROUND OF THE INVENTION

1. Field of the Invention

This invention relates generally to means for cylindrically diffusing energy from an optical wave guide, and more particularly, to a cylindrical diffuser tip for an optical fiber useful for performing Photodynamic Therapy in the treatment of tumors inducing hyperthermia or performing both percutaneous and intraoperative angioplasty.

2. Description of the Prior Art

Photodynamic treatment of tumors using hematoporphyrin derivatives requires that a tumor under treatment be irradiated with light usually around, but not limited to, a wavelength of 630 nanometers generally from a laser. A short time prior to irradiation, the patient is injected with a photo-sensitive compound which accumulates in the vascular stoma of the tumor and in cells. Subcutaneous tumors greater than 0.5 cm thick, also referred to herein as interstitial tumors, undergoing this treatment require the use of optical fibers to guide the light from the source to the treatment area. In the case of many tumors, the outlet termination of the fiber is inserted directly into the tumor. In other cases, where the tumor is located in passages, for example endobronchial tumors, the optical fiber termination is positioned intraluminally in close proximity to the tumor. Efforts have been directed in recent years to developing suitable fiber terminations for the delivery of a uniform, predictable dosage of effective irradiation to a large volume of tumor tissue.

Considerable radiation must be transmitted to kill large tumor masses by photo irradiation and the required radiation can cause overheating, especially if it is concentrated in too small a region. This causes problems in delivering radiant energy out of the end of a normal blunt ended or flat cut optical fiber, making a small hot spot which may lead to excessive heating, carbonization and necrosis of the adjacent tissue making it opaque to transillumination. Thermal sources such as xenon arc lamps also pose difficulties in transmitting adequate radiation to deep-seated tumors because non-coherent sources cannot be coupled efficiently to reasonable small optical fibers for delivery to the tumor. Problems of distributing radiation uniformly throughout the region of a tumor to be killed are also formidable.

There are several ways that the cylindrical diffusion of radiant energy from an optical fiber core can be accomplished. One way is to choose a ratio of the indices of refraction between the outer cladding and the core region of the optical fiber so that internal reflection within the core region is substantially less than total. This causes light to radiate outward through the side of the core region to emerge through (a preferably transparent) cladding.

Another way is to alter the interface between the fiber optic core and cladding to increase side radiation. Texturing the outer surface of the core region to provide a ground glass effect is one method commonly used. Another is positioning or embedding light scattering elements such as tiny particles at the surface of the fiber optic core near the interface with the cladding. Light scattering particles can also be imbedded throughout the cladding to enhance the side delivery of radiation. Combinations of these measures are also possible.

For example, Chapman in United Kingdom patent GB2154761A (issued Sep.11, 1985), which is incorporated herein by reference, describes an optical fiber for use in Photodynamic Therapy wherein the fiber comprises a central core material enveloped by a special two-layer cladding. The cladding comprises an inner cladding of a low refractive index material and an outer cladding. The fiber, being adapted to be coupled to a laser beam has an output end portion which has a tapered core region which is surrounded by a diffusing medium. Light emerging from the tapered core region undergoes scattering.

In one preferred embodiment, Chapman's core is of circular cross section and the diameter of the core in the tapered region decreases uniformly to an end most point over a length of between 5 and 15 millimeters. In a further preferred embodiment, Chapman describes a diffusion medium comprising a transparent resin material, which contains fine particulate reflective or refractive matter.

Clark, in U.S. Pat. No. 4,336,809 (issued Jun. 29, 1982) describes a tissue photo irradiation system for use with hematoporphyrin dyes and derivatives thereof. In Clark's system he describes the use of an optical needle which serves as a linear radiator or a cylindrical diffuser and which can be coupled to an optical fiber by means of a conventional optical coupler. Clark's needle includes a fiber optic core that is generally internally reflecting. The core is surrounded by a cladding as generally known; but in an end region a different cladding surrounds the core to make it into a radiator instead of an internally reflecting transmitter.

Production of a controllable level of temperature elevation or hyperthermia at pre-selected locations in volumes of tissue has been found to be of significant therapeutic value in the treatment of patients with cancer. In particular, hyperthermia may, in some cases, have a synergistic effect when used in conjunction with Photodynamic Therapy for treating tumors or performing angioplasty. At the high power levels required for hyperthermia or hyperthermia plus Photodynamic Therapy, high peak intensities or hot spots can lead to excessively high temperatures causing unintentional tissue damage. It is, therefore, desirable to distribute the illuminating energy evenly within the target volume to achieve uniform temperature distributions.

The present fiber optic cylindrical diffuser tip technology is limited in clinical applications due to the following:

a) The underlying fiber optic is weakened by mechanical processing during manufacturing of the cylindrical diffusing tip;

b) The weakened fiber optic limits the flexibility of the finished cylinder diffuser to the point of sole quasi-rigid usage (very limited endoscopic use);

c) Output sensitivity of prior art cylindrical diffuser tips to input beam divergence causes extreme variability in the output intensity distribution.

d) A non-uniform output intensity distribution makes treatment dosimetry uncertain and clinical results inconsistent;

It is desirable, therefore, to provide a cylindrical diffuser for use as a termination on an optical fiber which overcomes most or all of the limitations stated above.

SUMMARY OF THE INVENTION

One object of this invention is to provide a diffusion tip for an optical fiber which enables the cylindrical diffusion of radiant energy from the fiber uniformly both radially and along the length of the tip.

Another object of this invention is to provide a cylindrical diffusion tip for an optical fiber which is flexible.

Yet a further object of this invention is to provide a diffuser tip for an optical fiber which tip avoids high intensity non-uniform distribution of light energy commonly referred to as hot spots.

Yet a further object is to provide an optical fiber cylindrical diffusion tip for use in Photodynamic Therapy treatment of tumors that efficiently and uniformly cylindrically diffuses transmitted light and which diffuser tip has a maximum diameter substantially the same as that of the optical fiber's protective jacket.

Still another object of this invention is to provide an optical fiber diffuser tip which is useful for the treatment of atheromas in angioplasty.

Yet another object of this invention is to provide a terminal diffuser tip for an optical fiber useful for inducing hyperthermia in selected target tissue.

A further advantage of the termination tip of the present invention is that it is input mode independent. That is, the distribution of light out of the diffuser is independent of the coupling mode.

Accordingly, the present invention teaches the use of a diffusion tip in which a conventional optical fiber (with cladding) is terminated by abutting it with a silicone fiber core of diameter slightly greater than that of the optical fiber yet less than the outer diameter of the fiber jacket. On top of this silicone fiber terminus a layer of silicone containing a scatterer such as alumina is coated so that the outer coating has an outer diameter approximately equal to the outer diameter of the fiber optic jacket. The flexibility of the tip depends upon the durometer of the silicone used for making the silicone fiber and in general is very flexible. This flexibility may be altered by the insertion over the tip of a PFA or other plastic tubing which provides some rigidity and support to the flexible tip. The tubing and the silicone tip can be cut at angles for surgical application.

A DESCRIPTION OF THE PREFERRED EMBODIMENT

Figure 1:
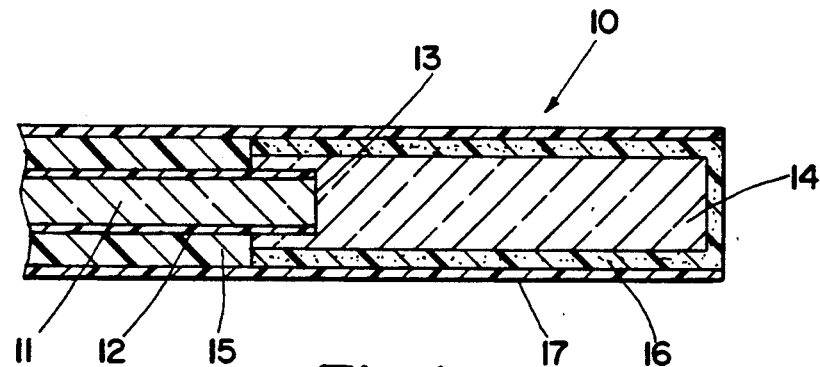
FIG. 1 is a schematic cutaway view of a silicone diffuser tip of the present invention.

A preferred embodiment of the optical fiber cylindrical diffuser tip of the present invention is indicated generally at 10 in FIG. 1. A standard optical fiber consisting of a core 11 and cladding 12 has a blunt distal end indicated at 13. A silicone tip 14 has a proximal end which is recessed to accommodate the distal end 13 of optical fiber core 11. In practice, the outer diameter of the silicone tip is greater than the outer diameter of the optical fiber core 11 plus clodding 12 but less than the outer diameter of the jacket 15. The silicone tip 14 may be any length but is preferably between 0.5 and 5 cm for Photodynamic Therapy irradiation of tumors.

After the silicone tip 14 is affixed to the optical fiber core, a second layer 16 consisting of silicone containing a scatterer is coated over the silicone tip by injection molding or dipping the silicone fiber into a suspension containing a scatterer such as diamond dust, Ti 02 or alumina in uncured silicone. The scattering layer 16 may then be vulcanized to the silicone tip by curing at an elevated temperature as is well known in the art. The diffuser tip thus obtained is, however, extremely flexible and, in practice, it is desirable to stiffen the fiber by the insertion of an optically transparent tubing 17 over the silicone tip.

The choice of material and wall thickness of the tubing 17 will ultimately determine the flexibility of the diffuser tip. The distribution of scattered light emanating from the silicone diffuser tip can be controlled by varying the concentration of scatterer in the silicone.

Figure 2:
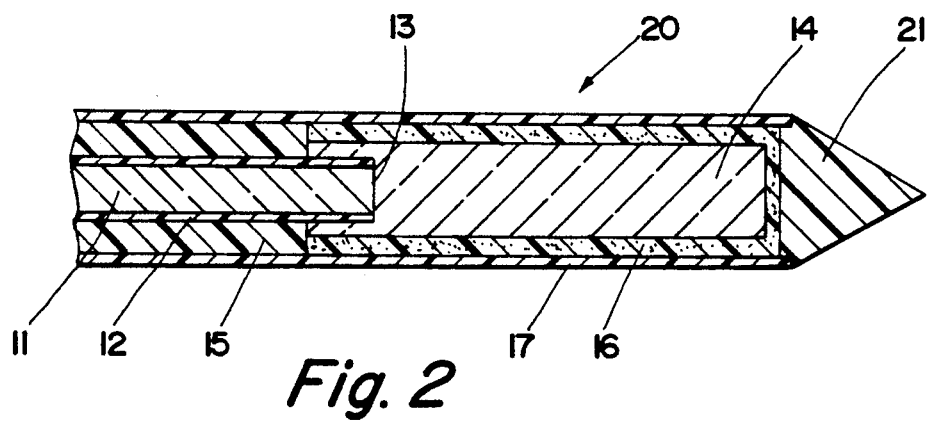
FIG. 2 is a cutaway schematic view of one embodiment of the diffusion tip showing a pointed tip to facilitate insertion through tissue.

Turning now to FIG. 2 a diffuser tip, generally indicated at 20, for use in irradiating interstitial tumors, is similar to the diffuser tip 10 but has a sharp pointed tip 21 enabling the tip to be pushed into and through tissue with or without the aid of a cannula. For interstitial use, it is desirable that the tip have as small an outer diameter as possible to facilitate penetration to the tumor. This interstitial cylindrical diffusion tip is concurrently made by bonding the silicone tip 14 to the optical fiber core 11 and cladding 12. Once cured, the tubular tip jacket 17 may be slipped over the core jacket 15 and pushed up the fiber beyond the optical fiber's distal end 13. The scattering layer 16 may then be applied as before and while the uncured silicone layer is still wet, the tip jacket 17 sleeve is pulled toward the tip 21 of the diffuser until it projects past the distal end 14 tip of the silicone tip. A conical translucent or opaque piercing tip 21 is then pressed into the uncured scattering layer and the assembly is allowed to cure.

It is important that the silicone used in both the fiber and the scattering layer be free of bubbles. This may be facilitated by applying a vacuum to the uncured silicone prior to use. Optical quality silicone, available from McGhan NuSil Corporation, Carpinteria, Calif., Catalog No. CF1-6755 is suitable for the construction of such tips.

Figure 3:
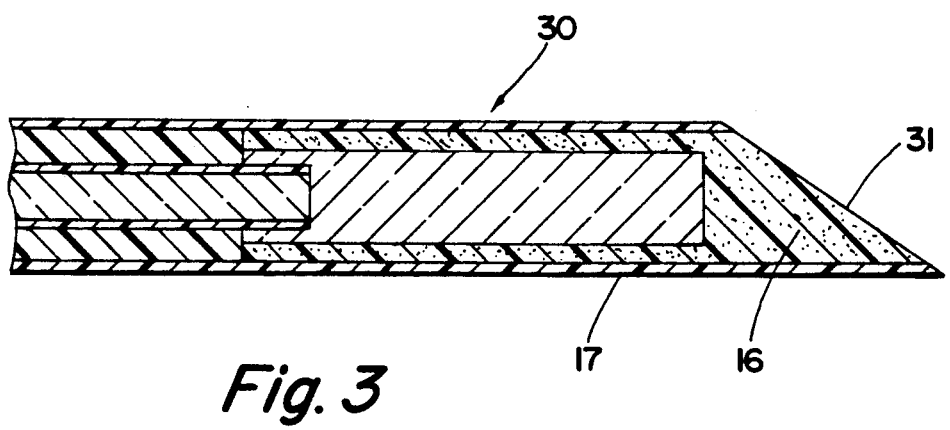
FIG. 3 shows a cutaway schematic view of a further embodiment of the diffusion tip having a beveled tip useful for interstitial illumination or surgery.
Figure 4:
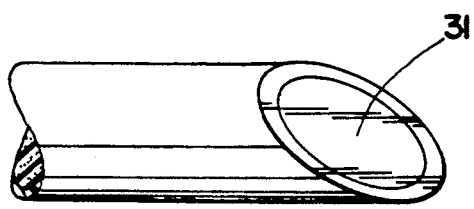
FIG. 4 is an isometric close-up view of the cylindrical diffuser tip of FIG. 3.

A further advantage of using a tip jacket 17 with the flexible silicone tip and scattering layer is the ability to shape the distal end of the tip jacket 17 into a piercing or cutting tool suitable for insertion into tissue or for performing laser surgery. FIG. 3 shows such an interstitial cylindrical diffuser generally indicated at 30 wherein the tip jacket 17 and scattering layer 16 of the diffuser 31 has been beveled to form a cutting blade which is shown in greater detail in FIG. 4. The sharp tip 31 can be used to cut through tissue.

Figure 5:
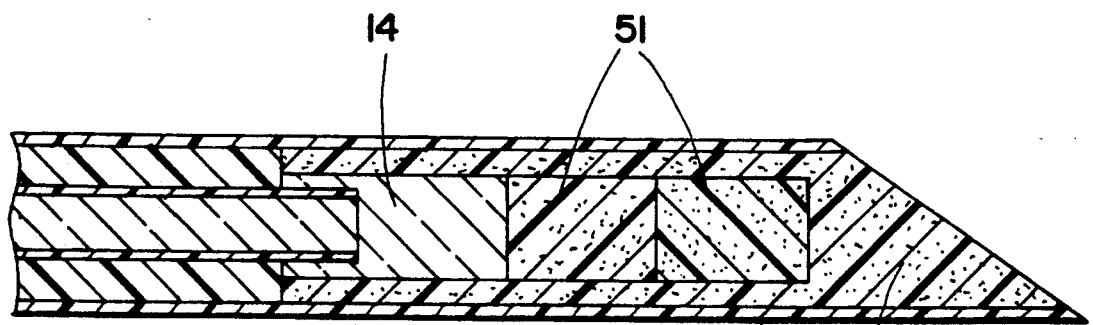
FIG. 5 is a cutaway side view of the diffuser tip of FIG. 3 in which the silicone tip is molded onto the optical fiber in three stages; each stage having a greater concentration of scatterer than the previous one.
Figure 6:
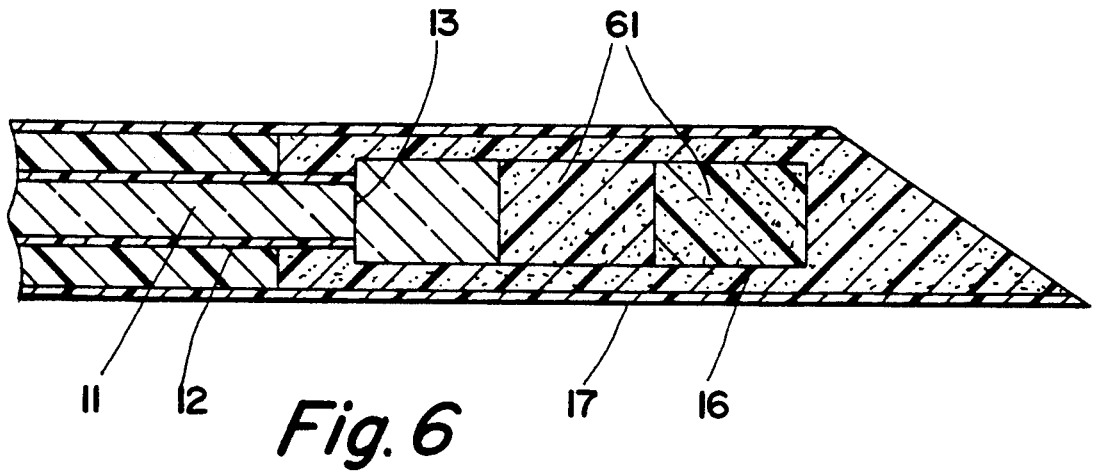
FIG. 6 is similar to FIG. 5 except that the silicone diffuser tip comprises three separate silicone plugs each having a different concentration of scatterer and not molded to the fiber.

Turning now to FIG. 5 and FIG. 6, a second and third preferred embodiment of the silicone diffuser tip of the present invention is shown in which the scattering centers are incorporated into the silicone tip 51 as well as in the scattering layer 16. In FIG. 5, the inner silicone tip is molded onto the optical fiber in three stages; each stage with a greater concentration of scatterer than the previous one. A stepwise concentration gradient of scattering centers is thereby achieved which may be varied to customize the intensity distribution of the diffused light for particular applications. The number of stages may be made greater if desired to achieve a smooth, nearly continuous variation in the concentration of scatterer along the tip. Alternatively, as shown in FIG. 6, silicone plugs 61 containing various concentrations of a suitable scatterer may be molded within the tubular scattering layer 16 to form a diffuser tip which tip may then be inserted over the distal end 13 of the optical fiber core 11 and cladding 12 and held firmly in place against the end of the optical fiber by tip jacket 17.

Figure 7:
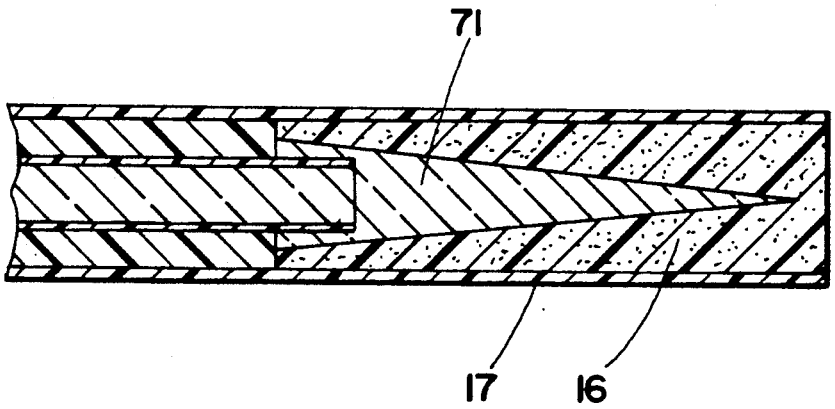
FIG. 7 is a cutaway side view of a diffuser tip of the present invention in which the silicone tip abutting the end face of the optical fiber is tapered.

FIG. 7 shows yet another preferred embodiment of the present invention in which the silicone tip 71 is tapered. As the optically transparent central core of the silicone tip decreases in diameter, the exiting laser light encounters a greater number of scatterers in the scattering layer 16 before exiting the tip jacket 17 The intensity distribution of the cylindrically diffused light will be smoother than with stepwise concentration gradients encountered by the light as it enters the plugs containing various concentrations of scatterers as shown in FIGS. 5 and 6.

As mentioned earlier, sensitivity of the output of prior art cylindrical diffuser tips to input beam divergence causes extreme variability in the output intensity distribution. The distribution of light emanating from the diffuser tip of the present invention is substantially independent of input couping mode.

The foregoing embodiments of the optical fiber cylindrical diffuser tip are offered by means of example. The invention should not be limited to the specific embodiment presented herein but only by the scope of the claims appended hereto.

We claim:

1. A method for destroying tissue by means of Photodynamic Therapy comprising the steps of:
   (a) introducing suitable photosensitive molecules into or around the tissue cells; and
   (b) illuminating said photosensitive molecules by means of a cylindrical diffuser tip to deliver an amount of light energy to said photosensitive molecules sufficient to effect the destruction of said tissue, said diffuser tip comprising, in combination,
   (i) an optical fiber and (ii) a terminus, said optical fiber comprising an optically transmissive first core surrounded by a layer of cladding and an outer sheath, said optical fiber having a tip portion in which tip portion the sheath is removed to expose the cladding; said terminus comprising a second core consisting of a substantially transparent elastomer, a first layer of said elastomer concentrically surrounding said second core, said first layer containing light-scattering centers embedded therein, and a second layer of a transparent plastic concentrically surrounding said first layer, said second layer providing means for controlling the strength and flexibility of said diffuser tip, and wherein said second core has a diameter equal to greater than the diameter of the tip portion of the optical fiber and the tip portion of the optical fiber extends into, and is enveloped by, at least a portion of said second core.

2. The method for destroying tissue by means of Photodynamic Therapy set forth in claim 1 wherein said tissue comprise tumor cells.

3. A method of treating atherosclerotic plaque in the wall of a blood vessel comprising the steps of:
   (a) introducing a photosensitive compound into the plaque; and,
   (b) insertion of an optical fiber into the blood vessel, said optical fiber having an optically transmissive core surrounded by a layer of cladding and an outer sheath, said optical fiber having a tip portion in which the sheathing has been removed to expose the cladding, said optical fiber tip portion extended into a diffuser tip, said diffuser tip comprising a cylindrical second core of a substantially transparent elastomer, a first layer of said elastomer concentrically surrounding said second core, said first layer containing light-scattering centers embedded therein, and a second layer of a transparent plastic concentrically surrounding said first layer, said second layer providing means for controlling the strength and flexibility of said diffuser tip and wherein said second core has a diameter equal to or greater than the diameter of the tip portion of the optical fiber and the tip portion of the optical fiber extends into and is enveloped by at least a portion of said second core of said diffuser tip.
   (c) irradiating the plaque with a wavelength suitable for activating said photosensitive compound; and,
   (d) delivering sufficient light energy to said photosensitive compound to cause necrosis of the atherosclerotic tissue in the wall of the blood vessel.

4. A diffusing optical fiber for providing cylindrical distribution of light to a target, said diffusing optical fiber comprising, in combination, a fiber portion and a diffuser tip portion, said fiber portion consisting of an optical fiber having a cylindrical optically transmissive first core, a cylindrical cladding surrounding said first core and a cylindrical outer sheath surrounding said cladding; said fiber portion having a distal end with a portion of the outer sheath removed to expose the cladding, said diffuser tip portion further comprising:
   (a) a cylindrical second core of a transparent elastomer; and
   (b) a first layer of said elastomer concentrically surrounding said second core, said first layer containing light scattering centers embedded therein; and,
   (c) a second layer of transparent plastic concentrically surrounding said first layer, said second layer enclosing the diffuser tip portion thereby providing means for controlling the strength and flexibility of the diffuser tip portion;

the second core having a diameter equal to or greater than the distal tip of the fiber portion and at least a portion of said second core enveloping the distal tip of the fiber portion.

5. The diffusing optical fiber of claim 4 wherein said second core comprises a transparent elastomer with light scattering centers embedded therein.

6. The diffuser tip of claim 5 wherein said elastomer is silicone.

7. The diffuser tip of claim 5 wherein the concentration of said scattering centers embedded in said core increases along the length of said core in the direction of light transmission.

* * * * *